(12) United States Patent
Linder et al.

(10) Patent No.: US 8,116,865 B2
(45) Date of Patent: Feb. 14, 2012

(54) DEFIBRILLATION SHOCK OUTPUT CIRCUIT

(75) Inventors: William J. Linder, Golden Valley, MN (US); Hari Sree, Plymouth, MN (US)

(73) Assignee: Cardiac Pacemarkers, Inc., St. Paul, MN (US)

( * ) Notice: Subject to any disclaimer, the term of this patent is extended or adjusted under 35 U.S.C. 154(b) by 486 days.

(21) Appl. No.: 12/332,497

(22) Filed: Dec. 11, 2008

(65) Prior Publication Data

US 2009/0157132 A1 Jun. 18, 2009

Related U.S. Application Data

(60) Provisional application No. 61/007,637, filed on Dec. 13, 2007.

(51) Int. Cl.
*A61N 1/39* (2006.01)
(52) U.S. Cl. .................................. 607/5; 607/6
(58) Field of Classification Search ........................ None
See application file for complete search history.

(56) References Cited

U.S. PATENT DOCUMENTS

| | | | |
|---|---|---|---|
| 4,998,531 A | 3/1991 | Bocchi et al. | |
| 5,591,211 A | 1/1997 | Meltzer | |
| 5,645,572 A * | 7/1997 | Kroll et al. ................ | 607/5 |
| 5,723,969 A | 3/1998 | Archer et al. | |
| 5,733,309 A * | 3/1998 | Kroll et al. ................ | 607/5 |
| 5,772,689 A | 6/1998 | Kroll | |
| 5,800,461 A | 9/1998 | Menken et al. | |
| 5,830,236 A | 11/1998 | Mouchawar et al. | |
| 6,175,765 B1 | 1/2001 | Sullivan et al. | |
| 6,233,483 B1 | 5/2001 | Causey, III et al. | |
| 6,311,087 B1 | 10/2001 | Vane et al. | |
| 6,421,563 B1 | 7/2002 | Sullivan et al. | |
| 6,438,420 B1 | 8/2002 | Thompson | |
| 6,456,877 B1 | 9/2002 | Fishler | |
| 6,477,413 B1 | 11/2002 | Sullivan et al. | |
| 6,484,056 B2 | 11/2002 | Fisher et al. | |
| 6,522,920 B2 | 2/2003 | Silvian et al. | |
| 6,539,258 B1 | 3/2003 | Sullivan et al. | |
| 6,647,294 B2 | 11/2003 | Vane et al. | |
| 6,668,193 B2 | 12/2003 | Ware et al. | |
| 6,714,818 B1 | 3/2004 | Fishler et al. | |
| 6,745,073 B1 | 6/2004 | Kroll | |

(Continued)

FOREIGN PATENT DOCUMENTS

EP 1530983 A2 5/2005

(Continued)

OTHER PUBLICATIONS

"International Application Serial No. PCT/US2008/013616, International Search Report mailed Jun. 17, 2009", 5 pgs.

(Continued)

*Primary Examiner* — Carl H Layno
*Assistant Examiner* — Paula J Stice
(74) *Attorney, Agent, or Firm* — Schwegman, Lundberg & Woessner, P.A.

(57) ABSTRACT

This document discusses, among other things, techniques for generating and delivering a high voltage defibrillation shock using an implantable cardiac rhythm management device. An output energy delivery bridge can be programmed to provide desired shock vectors or polarities. A bootstrapped fully solid-state switch control voltage generation circuit is described. Automatic polarity or vector reconfiguration embodiments are described, such as in response to an unsuccessful attempt to convert the heart to a normal rhythm.

21 Claims, 4 Drawing Sheets

U.S. PATENT DOCUMENTS

| | | |
|---|---|---|
| 6,873,874 B2 | 3/2005 | Ware et al. |
| 6,954,669 B1 | 10/2005 | Fishler et al. |
| 6,963,773 B2 | 11/2005 | Waltman et al. |
| 6,968,230 B2 | 11/2005 | Waltman |
| 6,980,856 B2 | 12/2005 | Sullivan et al. |
| 7,096,063 B2 | 8/2006 | Wanasek et al. |
| 7,155,286 B1 | 12/2006 | Kroll et al. |
| 2004/0172066 A1 | 9/2004 | Wagner et al. |
| 2004/0254613 A1* | 12/2004 | Ostroff et al. .............. 607/5 |
| 2005/0165451 A1 | 7/2005 | Ware et al. |
| 2010/0298897 A1 | 11/2010 | Chavan et al. |

FOREIGN PATENT DOCUMENTS

| | | |
|---|---|---|
| EP | 1535645 A1 | 6/2005 |
| WO | WO-95/03087 A1 | 2/1995 |
| WO | WO-2005/092437 A1 | 10/2005 |
| WO | WO-2009/078942 A2 | 6/2009 |

OTHER PUBLICATIONS

"International Application Serial No. PCT/US2008/013616, Written Opinion mailed Jun. 17, 2009", 8 pgs.

* cited by examiner

DEFIBRILLATION SHOCK OUTPUT CIRCUIT

CROSS-REFERENCE TO RELATED APPLICATION

This application claims the benefit of U.S. Provisional Application No. 61/007,637, filed on Dec. 13, 2007, under 35 U.S.C. §119(e), which is hereby incorporated by reference.

TECHNICAL FIELD

This patent application pertains generally to implantable cardiac rhythm management devices and more particularly, but not by way of limitation, to a programmable output energy delivery bridge.

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a subject. For example, an implantable defibrillator/pacer is typically configured as an implantable defibrillator with backup pacing capability. Such devices are intended to serve patients having a history of previous ventricular or atrial tachyarrhythmia episodes. Ventricular arrhythmias include ventricular tachyarrhythmia (VT) and dangerous and life-threatening ventricular fibrillation (VF), referred to collectively herein as VT/VF. VT/VF is typically treated with antitachyarrhythmia pacing (ATP) therapy or a defibrillation countershock.

SUMMARY OF THE DISCLOSURE

Examples of techniques for generating and delivering a high voltage defibrillation shock using an implantable CRM device are disclosed herein. An output energy delivery bridge can be programmed to provide desired shock vectors or polarities in some examples. A bootstrapped fully solid-state switch control voltage generation circuit is described. Automatic polarity or vector reconfiguration embodiments are described according to some examples, such as in response to an unsuccessful attempt to convert the heart to a normal rhythm.

Example 1 includes an implantable medical device for delivering electric therapy to a heart of a patient comprising a voltage source, a first switch circuit, and a bridge circuit. The first switch circuit comprises a first node and a second node. The first node is coupled to a first terminal of the voltage source. The bridge circuit is coupled to the second node and to a second terminal of the voltage source. The bridge circuit is configured to connect to a first electrode and a second electrode. The first and second electrodes are configured to be implanted in or near the heart. The bridge circuit is also configured to deliver a first polarity energy to the heart using the first and second electrodes in a first mode and an opposite polarity energy to the heart using the first and second electrodes in a second mode.

In Example 2, the first switch circuit of Example 1 is optionally configured to control a timing of the delivery of the first polarity energy and the opposite polarity energy.

In Example 3, the implantable medical device of any of Examples 1-2 optionally includes the first electrode. The first electrode comprises a can electrode.

In Example 4, the implantable medical device of any of Examples 1-2 optionally includes the first electrode. The first electrode comprises an atrial coil electrode.

In Example 5, the implantable medical device of any of Examples 1-4 optionally include the second electrode. The second electrode comprises a ventricular coil electrode.

In Example 6, the bridge circuit of any of Examples 1-5 optionally includes a second switch circuit, a third switch circuit, a fourth switch circuit, and a fifth switch circuit. The second switch circuit is coupled to the second node and configured to be connected to the first electrode. The third switch circuit is coupled to the second node and configured to be connected to the second electrode. The fourth switch circuit is coupled to the second terminal and configured to be connected to the first electrode. The fifth switch circuit is coupled to the second terminal and configured to be connected to the second electrode. The bridge circuit is configured to deliver the first polarity energy when the third and fourth switch circuits are closed, and to deliver the opposite polarity energy when the second and fifth switch circuits are closed.

In Example 7, the second, third, fourth, and fifth switch circuits of Example 6 optionally comprise thyristors.

In Example 8, the second and fourth switch circuits of any of Examples 6-7 are optionally stacked substantially adjacent to each other.

In Example 9, the implantable medical device of any of Examples 6-8 optionally comprises a sixth switch circuit and a seventh switch circuit. The sixth switch circuit is coupled to the second node and configured to be connected to a third electrode. The third electrode is configured to be implanted in or near the heart. The seventh switch circuit is coupled to the second terminal and is configured to be connected to the third electrode. The bridge circuit is configured to deliver a third energy to the heart when the fourth and sixth switch circuits are closed, and to deliver a fourth energy to the heart when the second and seventh switch circuits are closed.

In Example 10, the bridge circuit of Example 9 is optionally configured to deliver the first polarity energy concurrently with the third energy.

In Example 11, the system of any of Examples 9-10 is optionally configured to deliver the opposite polarity energy concurrently with the fourth energy.

In Example 12, the switch circuit of any of Examples 1-11 optionally comprises a bipolar junction transistor (BJT).

In Example 13, the switch circuit of Example 12 optionally comprises a first control terminal, a drive voltage capacitor, a resistive element, a second diode, and a firing circuit. The first control terminal is coupled to a first diode, the first diode coupled to a third node. The drive voltage capacitor is coupled to the third node and to the second node. The resistive element is coupled to the third node and to a fourth node. The second diode is coupled to the second node and the fourth node. The firing circuit is coupled to the fourth node. A base of the BJT is coupled to the fourth node, a collector of the BJT is coupled to the first node, and an emitter of the BJT is coupled to the second node. The first control terminal is configured to provide a first controlled voltage to charge the drive voltage capacitor in a first stage.

In Example 14, the firing circuit of Example 13 optionally includes a second control terminal coupled to a second capacitor and to a gate of a field effect transistor (FET). The second capacitor is coupled to a drain of the FET and to the fourth node. A source of the FET is coupled to a ground voltage. The second control terminal is configured to provide a second controlled voltage to activate the BJT in a second stage.

Example 15 includes a method of delivering defibrillation energy to a heart of a patient using an implanted medical device including providing a voltage source, controlling a bridge circuit, and closing a switch circuit. The bridge circuit is coupled to a first terminal of the voltage source such that the bridge circuit is in a first mode. The switch circuit is coupled to a second terminal of the voltage source and to the bridge circuit, such that a first polarity energy is provided to the heart through the bridge circuit.

In Example 16, closing the switch circuit in Example 15 optionally includes comprises charging a drive voltage capacitor coupled to a gate and an emitter of a transistor. The transistor comprises a collector coupled to the second terminal of the voltage source and the emitter coupled to the bridge circuit. Closing the switch circuit also includes causing the drive voltage capacitor to provide a voltage to turn on the transistor.

In Example 17, the method of Example 15 optionally includes the switch circuit is a first switch circuit. Controlling a bridge circuit such that the bridge circuit is in a first mode in Example 15 optionally includes closing a second switch circuit coupled to the first terminal and to a first electrode implanted in or near the heart, and closing a third switch circuit coupled to a second electrode implanted in or near the heart and coupled to the first switch circuit.

In Example 18, controlling a bridge circuit such that the bridge circuit is in a first mode in Example 17 optionally includes closing a fourth switch circuit coupled to a third electrode implanted in or near the heart and coupled to the first switch circuit.

In Example 19, the method of any of Examples 15-18 optionally include opening the switch circuit, controlling the bridge circuit such that the bridge circuit is in a second mode, and closing the switch circuit such that an opposite polarity energy is provided to the heart through the bridge circuit.

In Example 20, the method of Example 19 optionally includes determining whether an arrhythmia is present in the heart before delivering the first polarity energy, and determining whether the arrhythmia remains present before delivering the opposite polarity energy.

Example 21 includes an implantable medical device. The implantable medical device includes a voltage source, means for controlling a bridge circuit coupled to the voltage source, and means for closing a first switch circuit coupled to the voltage source and to the bridge circuit such that a first polarity energy is provided through the bridge circuit.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
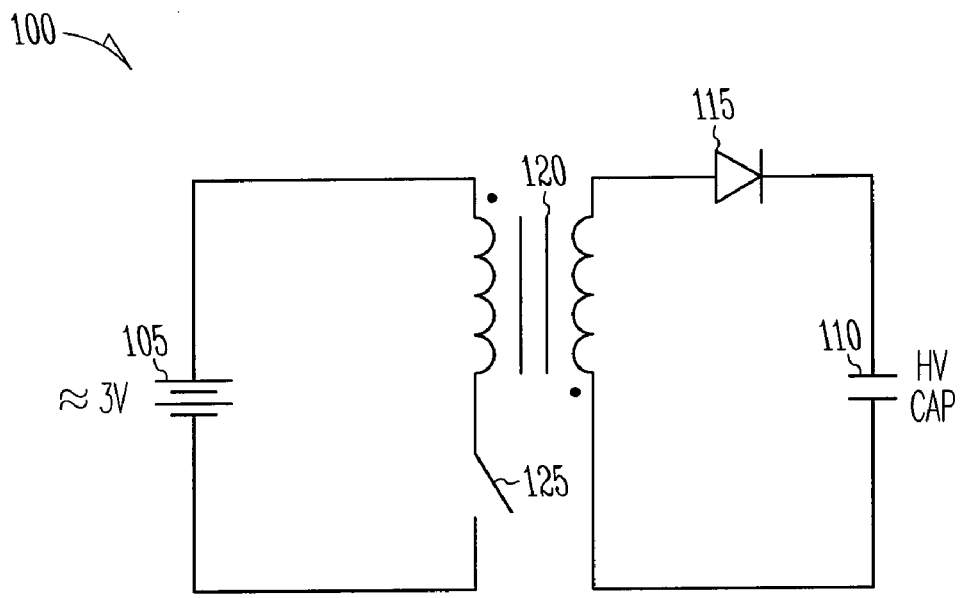
FIG. 1 is an example of a high voltage charging circuit for generating a high defibrillation voltage in an implantable cardiac function management device.

FIG. 1 is an example of a high voltage charging circuit 100 for generating a high defibrillation voltage (e.g., 40V-780V) in an implantable cardiac function management device. In this example, the high defibrillation voltage is stored on at least one high voltage capacitor 110 ("HV Cap"), and the particular defibrillation voltage depends on the desired shock energy (e.g., 0.1 J to 41 J). FIG. 1 shows an example of how this can be accomplished by using a flyback converter to transfer energy from the battery 105 (e.g., at about 3V) to the high voltage capacitor.

In FIG. 1, when the switch 125 (e.g., n-channel MOSFET) is closed, the current through the primary winding of the flyback transformer ramps up to a maximum value (e.g., about 9 amps). While this current is building, the diode 115 is reverse-biased, so no current flows in the secondary winding of the transformer 120. When the current reaches its desired peak value, the switch 125 is opened. When the switch 125 is opened, the output of the transformer 120 reverses, and the diode 115 becomes forward biased. The energy that was stored in the transformer 120 is then transferred to the high voltage capacitor 110. This can be repeated (e.g., at 10 microsecond cycles) until the capacitor 110 is charged to the desired voltage.

In certain examples, one or more bypass capacitors can be placed in parallel with the battery 105 to help source the peak current when the switch 125 is closed. In certain examples, the high voltage capacitor can be implemented as two separate capacitors in series, and each such series capacitor can be given its own secondary transformer winding. In certain examples, additional windings can be used, such as to supply the current used to meet the current demands associated with switching the switch in the primary winding path.

Figure 2:
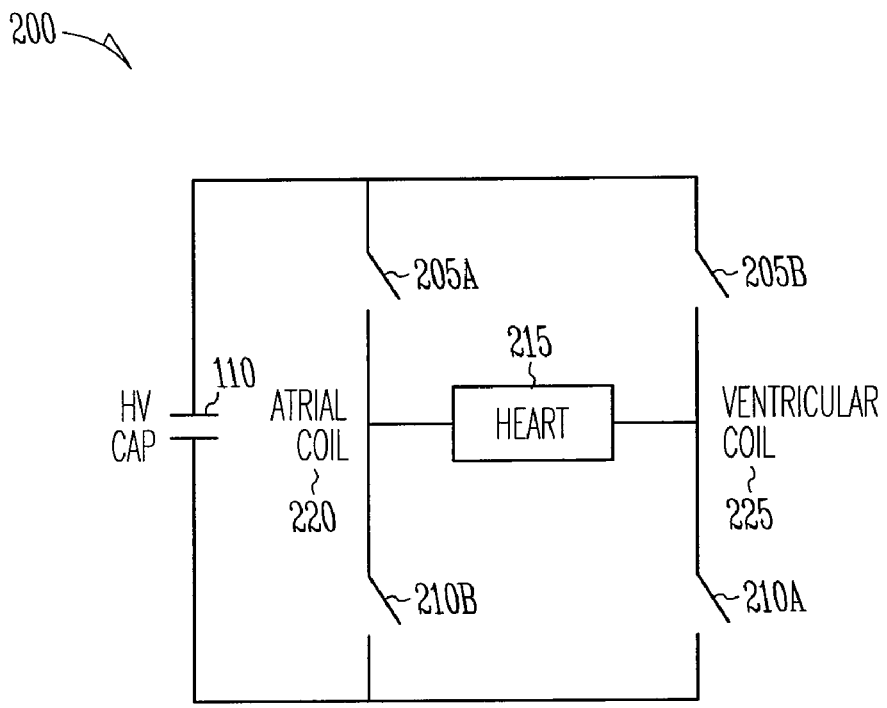
FIG. 2 is a drawing of an example of an H-bridge output bridge approach for delivering energy from the high voltage capacitor to the desired defibrillation electrodes, which are implanted within the patient receiving the defibrillation therapy.

FIG. 2 is a drawing of an example of an H-bridge output bridge approach for delivering energy from the high voltage capacitor to the desired defibrillation electrodes, which are implanted within the patient receiving the defibrillation therapy. Examples of such defibrillation electrodes are denoted as "atrial coil" 220 and "ventricular coil" 225 in FIG. 2. If it is desired that the atrial coil 220 be positive during a first phase of a two-phase (biphasic) defibrillation waveform, then the switches labeled 205A and 210A can be closed for phase 1. After phase 1, the switches labeled 205A and 210A can be opened. Then, the switches labeled 205B and 210B can be closed for phase 2, and then opened after phase 2. In a "hot can" configuration, the implantable defibrillator housing (which is sometimes referred to as the "can") provides a "can" electrode that is electrically connected (e.g., "shorted") to the atrial coil electrode 220. This can be accomplished, in certain examples, via a hard electrical connection (e.g., provided at manufacturing) in a header feed-through portion of the implantable defibrillator, where the atrial and ventricular coil electrodes are disposed on an intravascular leadwire that is electrically connected to the implantable defibrillator at the header. In a "cold can" configuration, the implantable defibrillator housing is not electrically connected to the atrial or ventricular coil electrodes.

One potential issue with the H-bridge configuration of FIG. 2 occurs when, for a particular one of phase 1 or phase 2, the top ("high side") switch is implemented as a thyristor, and the bottom switch is implemented as a field-effect transistor. In such an example, the transistor switch is essentially used for electrode selection, and the high side thyristor switching characteristic determines the rise and fall times of the switching. However, because the thyristor switches abruptly, the switching rise and fall times are not necessarily well-controlled by the high-side thyristor, and this could lead to complicated secondary circuit design or layout considerations, such as to avoid or deal with the effect of parasitic reactances during such abrupt switching.

Figure 3:
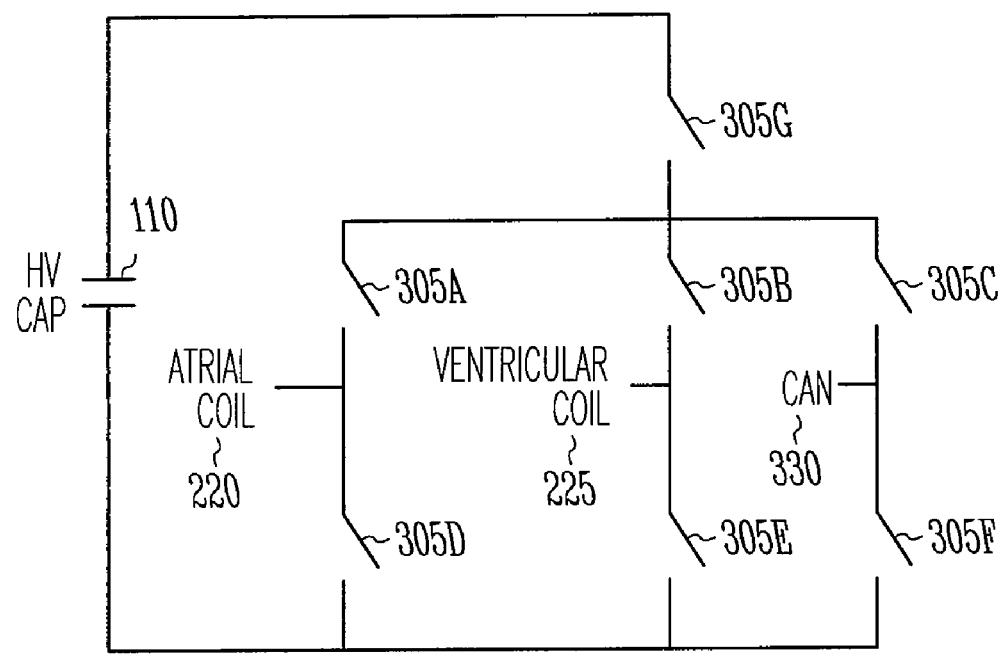
FIG. 3 is a schematic drawing illustrating generally an example of an alternative approach for delivering energy from the high voltage capacitor to the desired defibrillation electrodes, which are implanted within the patient receiving the defibrillation therapy.

FIG. 3 is a schematic drawing illustrating generally an example of an alternative approach for delivering energy from the high voltage capacitor to the desired defibrillation electrodes, which are implanted within the patient receiving the defibrillation therapy. Examples of such defibrillation electrodes are denoted as "atrial coil 220," "ventricular coil 225," and "can 330" in FIG. 3. Unlike the "hot can" example described above, with respect to FIG. 2, in the example of FIG. 3, that "can" electrode 330 can be selectively utilized (via switches 305C and 305F) rather than "hard-wired" (or not "hard-wired") at manufacturing.

In certain examples, the shock delivery circuit 300 of FIG. 3 can be used to provide at least three different defibrillation shock vectors: (1) Right Ventricular Coil 225 to Right Atrial Coil 220; (2) Right Ventricular Coil 225 to Right Atrial Coil 220 and Can 330; or (3) Right Ventricular Coil 225 to Can 330. An example of such shock vectors and corresponding switching configurations is described in Table 1.

TABLE 1

Example of Shock Vectors and Switch Operation

| Shock Vector | Switches closed during phase 1 | Switches closed during phase 2 |
| --- | --- | --- |
| RV coil to RA coil | 305A, E, G | 305B, D, G |
| RV coil to RA coil and CAN | 305A, C, E, G | 305B, D, F, G |
| RV coil to CAN | 305C, E, G | 305B, F, G |

Figure 4:
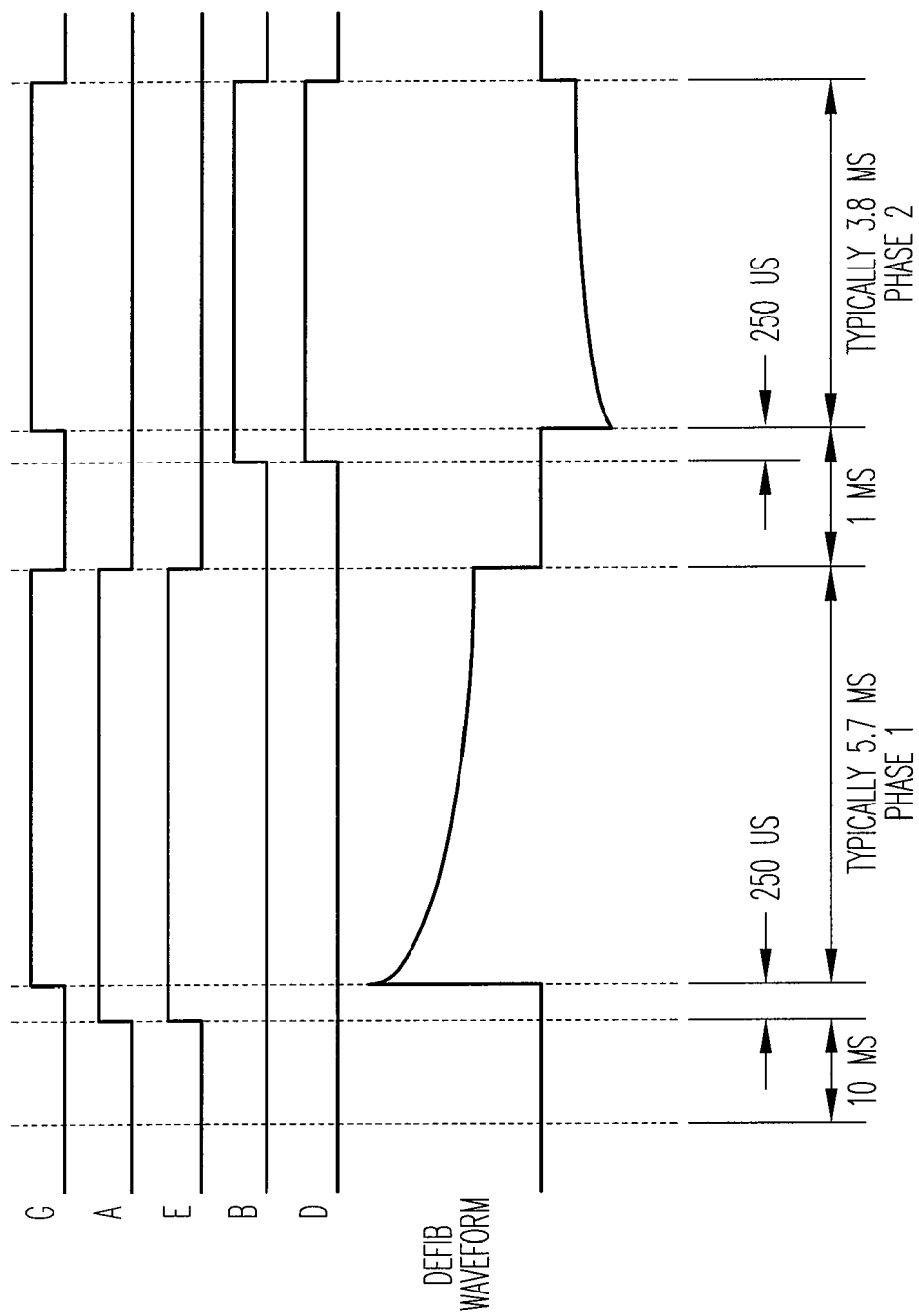
FIG. 4 shows an example of the timing for a RV coil to RA coil shock.

In certain examples, when a defibrillation shock is delivered, switches 305A-F are configured as desired at brief time period (e.g., 250 microseconds) before closing switch 305G. FIG. 4 shows an example of this timing for a 'RV coil 225 to RA coil 220' shock.

In FIG. 3, in certain examples, the switches 305A-F can be implemented as thyristors (such as by using remote gate thyristors (RGTs) or silicon controlled rectifiers (SCRs)), and the switch 305G is implemented as a transistor (such as an insulated gate bipolar transistor (IGBT). In certain examples, the topology shown in FIG. 3 permits the switches 305A and 305D to be stacked (e.g., switch 305A, which can include an RGT, stacked with switch 305D, which can include an SCR), also permits the switches 305B and 305E to be stacked (e.g., switch 305B, which can include an RGT, stacked with switch 305E, which can include an SCR), and also permits the switches 305C and 305F to be stacked (e.g., switch 305C, which can include an RGT, stacked with switch 305F, which can include an SCR), thereby saving space and reducing the size of the implantable cardiac function management device.

Figure 5:
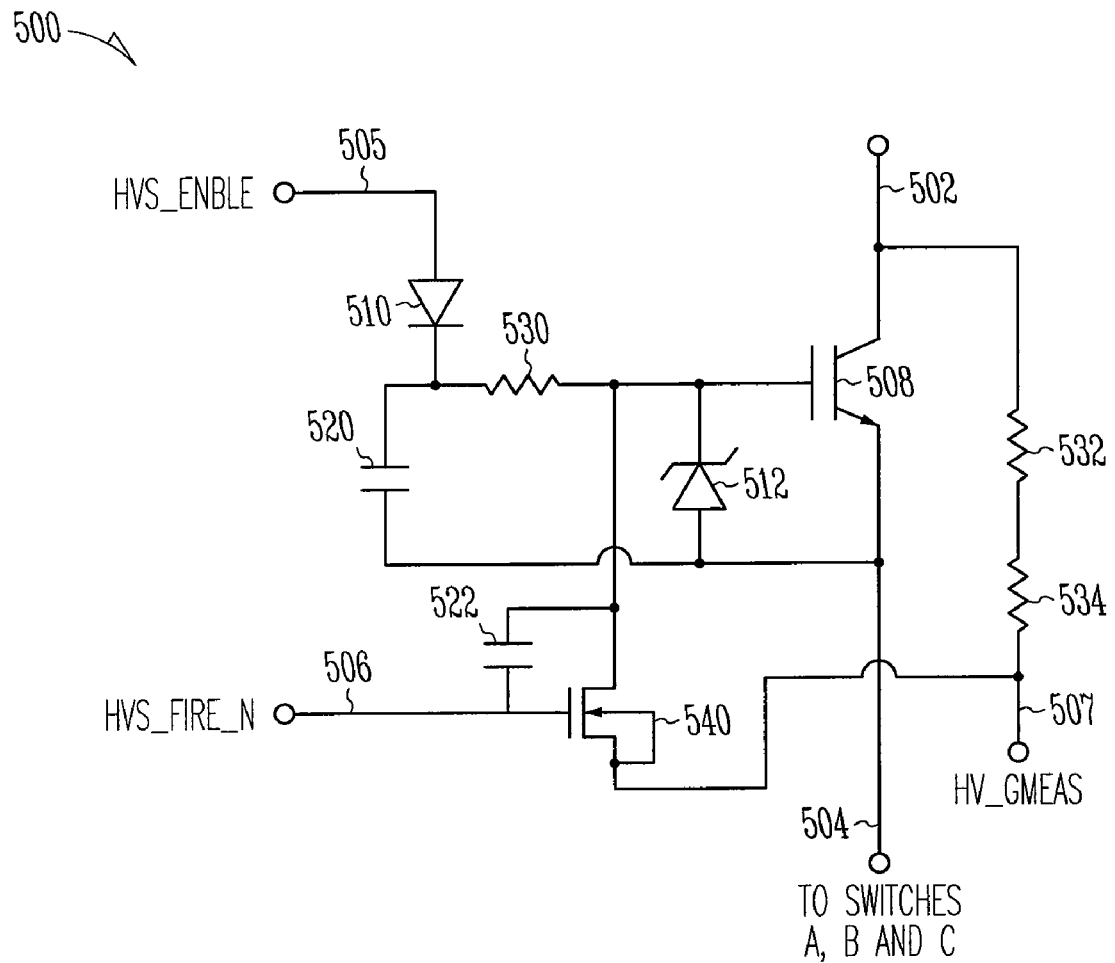
FIG. 5 is a schematic drawing illustrating generally an example of a switch circuit, such as for implementing switch 305G of FIG. 3.

FIG. 5 is a schematic drawing illustrating generally an example of a switch circuit 500, such as for implementing switch 305G of FIG. 3. In this example, a node 502 represents the connection between switch 305G of FIG. 3 to a terminal of the HV capacitor, as shown in FIG. 3. A node 504 represents the connection between the switch 305G of FIG. 3, and the common node of switches 305A, 305B, and 305C of FIG. 3.

Control of the switch 305G of FIG. 3 can be implemented, in FIG. 5, by three separate control signal inputs: (1) HVS_ENBLE at node 505, (2) HVS_FIRE_N at node 506, and (3) HVGMEAS at node 507. In an "idle" state, HVS_ENBLE is held "low" at 0V, HVS_FIRE_N is held "high" at 12V, and HVS_GMEAS is held "low" at 0V.

Turning "on" the switch 305G of FIG. 3 corresponds to turning "on" the corresponding n-channel insulating gate npn bipolar junction transistor (IGBT) 508 in FIG. 5. To prepare for turning on IGBT 508, a gate-emitter drive voltage can be stored across a capacitor 520 (e.g., 1.5 microFarads). This can be accomplished by transitioning HVS_ENBLE at node 505 to a "high" voltage of 12V. This forward-biases and turns-on a diode 510, thereby allowing current to flow through and charge up the capacitor 520. This same current also flows through a diode 512, which is forward-biased "on." This same current also flows through the drain-source conduction path of an n-channel field effect transistor (FET) 540, which is "on." This same current is then sunk at node 507 by the circuit providing the "low" 0V ground voltage at HV_GMEAS. During this time period, since the FET 540 is "on", there is a voltage of about 12V stored across a capacitor 522 (e.g., 10pF, rated for 1000V), which is located between the gate and drain terminals of the FET 540 (since the drain terminal of the FET 540 is at 0V and the gate terminal of the FET 540 is at 12V).

Next, turning "on" switch 305G of FIG. 3 corresponds to turning "on" the IGBT 508 in FIG. 5. Initially, the gate-emitter voltage of the IGBT 508 is close to 0V, such that the IGBT 508 is "off". To turn on the IGBJT 508, a control signal HVS_FIRE_N at node 506 is transitioned from a logic "high" at 12V to a logic "low" at 0V. Because of the voltage that was previously stored across the capacitor 522 during the above-described preparation phase, the voltage at the gate terminal of the IGBT 508 is at a voltage that is more negative than the about 11.5V at the node between 520 and 510 (e.g., the HVS_ENBLE voltage of 12V less a diode drop of about 0.5V). This causes a current to flow in a resistor 530 (e.g., 18 Kohms) to charge the capacitor 522 and to reverse-bias the diode 512 to be "off". The drive voltage that was previously stored across the capacitor 520 now effectively appears across the gate and emitter terminals of the IGBT 508. This turns the IGBT 508 "on." When the IGBT 508 turns on, the voltage at node 504 begins to rise toward the high voltage delivered by the high voltage capacitor at node 502. As the voltage at node 504 begins to rise, the voltage at the node between the capacitor 520 and the diode 510 follows suit, thereby reverse-biasing the diode 510. In this manner, a "bootstrap" voltage is provided at the node between 520 and 510 to provide sufficient drive voltage to the gate of IGBT 508 even as its emitter voltage rises toward the high voltage provided by the HV capacitor at node 502.

Moreover, in the above example, a well-controlled rise or fall time of the switching of the IGBT 508 can be established. The rise or fall time of the switching of the IGBT 508 can be established by delivering a controlled current at HVS-_FIRE_N to charge the capacitor 522 as the gate voltage of the IGBJT 508 is driven high by the voltage-follower like arrangement of the IGBT 508 described above. Moreover, since 522 is configured as a "Miller" capacitor between the fixed gate voltage and the widely swinging drain voltage of the FET 540, this can advantageously be used to provide a larger effective capacitance for controlling the switching rise or fall time of the IGBT 508, if desired. The switching time of the IGBT 508 will also be affected by the RC time constant formed by 530 and the gate capacitance of the IGBT 508.

The configuration described above with respect to FIGS. 3 and 5 also provides all solid-state control for performing the switching—without requiring any opticoupler, triggering transformer, floating supply, or transformer-coupled supply, as may be required by certain other approaches. This can reduce expense, circuit volume, and complications that may arise from such other approaches.

The configuration described above with respect to FIGS. 3 and 5 also has advantages over hard-wired "hot can" or "cold can" configurations described above since it allows flexibility in defibrillation waveforms. For example, Table 1 illustrates a shock vector from RV coil to RA coil by closing switches 305A, 305E, and 305G during phase 1, and then closing switches 305B, 305D, and 305G during phase 2. In another example, the polarity of this shock vector could be reversed by closing switches 305B, 305D, and 305G during phase 1, and then closing switches 305A, 305E, and 305G during phase 2. Similarly, the other waveform polarities can also be reversed by interchanging the switches closed in phase 1 with the switches closed in phase 2.

In a further example, automatic polarity reversal is implemented. For example, after each shock delivery, sensing circuits are used to determine whether the rhythm has successfully been converted from a tachyarrhythmia or fibrillation waveform to a normal waveform. If, after a specified number of attempts (e.g., 3 shocks), the heart has not been converted to a normal rhythm, then at least one subsequent attempt (e.g., the 4th shock) is performed using the opposite waveform polarity of the same shock vector. In other examples, different shock vectors or polarities are automatically used, such as when initial defibrillation shock attempts for that particular episode have been unsuccessful at obtaining a normal heart rhythm.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable medical device for delivering electric therapy to a heart of a patient, comprising:
   a defibrillation voltage source;
   a first switch circuit comprising a first node and a second node, the first node coupled to a first terminal of the voltage source;
   a bridge circuit coupled to the second node and to a second terminal of the voltage source, the bridge circuit configured to connect to a first electrode and a second electrode, the first and second electrodes configured to be implanted in or near the heart;
   wherein the bridge circuit is configured to deliver a first polarity energy to the heart using the first and second electrodes in a first mode, and the bridge circuit is configured to deliver an opposite polarity energy to the heart using the first and second electrodes in a second mode; and
   wherein closing the first switch circuit comprises charging a drive voltage capacitor coupled to a gate and an emitter of a transistor, the transistor comprising a collector coupled to the first terminal of the voltage source and the emitter coupled to the bridge circuit, and causing the drive voltage capacitor to provide a voltage to turn on the transistor.

2. The implantable medical device of claim 1, wherein the first switch circuit is configured to control a timing of the delivery of the first polarity energy and the opposite polarity energy.

3. The implantable medical device of claim 1, further comprising the first electrode, the first electrode comprising a can electrode.

4. The implantable medical device of claim 1, further comprising the first electrode, the first electrode comprising an atrial coil electrode.

5. The implantable medical device of claim 1, further comprising the second electrode, the second electrode comprising a ventricular coil electrode.

6. The implantable medical device of claim 1, the bridge circuit comprising:
a second switch circuit coupled to the second node and configured to be connected to the first electrode;
a third switch circuit coupled to the second node and configured to be connected to the second electrode;
a fourth switch circuit coupled to the second terminal and configured to be connected to the first electrode;
a fifth switch circuit coupled to the second terminal and configured to be connected to the second electrode; and
wherein the bridge circuit is configured to deliver the first polarity energy when the third and fourth switch circuits are closed, and wherein the bridge circuit is configured to deliver the opposite polarity energy when the second and fifth switch circuits are closed.

7. The implantable medical device of claim 6, wherein the second, third, fourth, and fifth switch circuits comprise thyristors.

8. The implantable medical device of claim 7, wherein the second and fourth switch circuits are stacked substantially adjacent to each other.

9. The implantable medical device of claim 6, further comprising:
a sixth switch circuit coupled to the second node and configured to be connected to a third electrode, the third electrode configured to be implanted in or near the heart;
a seventh switch circuit coupled to the second terminal and configured to be connected to the third electrode; and
wherein the bridge circuit is configured to deliver a third energy to the heart when the fourth and sixth switch circuits are closed, and wherein the bridge circuit is configured to deliver a fourth energy to the heart when the second and seventh switch circuits are closed.

10. The implantable medical device of claim 9, wherein the bridge circuit is configured to deliver the first polarity energy concurrently with the third energy.

11. The implantable medical device of claim 9, wherein the system is configured to deliver the opposite polarity energy concurrently with the fourth energy.

12. The implantable medical device of claim 1, wherein the switch circuit comprises a bipolar junction transistor (BJT).

13. The implantable medical device of claim 12, wherein the switch circuit comprises:
a first control terminal coupled to a first diode, the first diode coupled to a third node;
a drive voltage capacitor coupled to the third node and to the second node;
a resistive element coupled to the third node and to a fourth node;
a second diode coupled to the second node and the fourth node;
a firing circuit coupled to the fourth node; and
wherein a base of the BJT is coupled to the fourth node, a collector of the BJT is coupled to the first node, and an emitter of the BJT is coupled to the second node, and wherein the first control terminal is configured to provide a first controlled voltage to charge the drive voltage capacitor in a first stage.

14. The implantable medical device of claim 13, the firing circuit comprising:
a second control terminal coupled to a second capacitor and to a gate of a field effect transistor (FET); and
wherein the second capacitor is coupled to a drain of the FET and to the fourth node, and a source of the FET is coupled to a ground voltage, and wherein the second control terminal is configured to provide a second controlled voltage to activate the BJT in a second stage.

15. The implantable medical device of claim 1, further comprising a non-transitory tangible machine-readable medium including instructions that configure the implantable medical device to:
control the bridge circuit, such that the bridge circuit is in a first mode; and
close the first switch circuit, such that a first polarity energy is provided to the heart through the bridge circuit, wherein closing the first switch circuit comprises charging the drive voltage capacitor coupled to the gate and the emitter of the transistor comprising the collector coupled to the second terminal of the voltage source and the emitter coupled to the bridge circuit, and causing the drive voltage capacitor to provide a voltage to turn on the transistor.

16. The implantable medical device of claim 1, comprising a non-transitory tangible machine-readable medium including instructions that configure the implantable medical device to control the bridge circuit such that the bridge circuit is in a first mode, and comprising instructions that configure the implantable medical device to:
close a second switch circuit coupled to the first terminal and to a first electrode implanted in or near the heart; and
close a third switch circuit coupled to a second electrode implanted in or near the heart and coupled to the first switch circuit.

17. The implantable medical device of claim 16, comprising a non-transitory tangible machine-readable medium including instructions that configure the implantable medical device to control the bridge circuit such that the bridge circuit is in a first mode, and comprising instructions that configure the implantable medical device to:
control the bridge circuit such that the bridge circuit is configured to operate in the first that comprises closing a fourth switch circuit coupled to a third electrode implanted in or near the heart and coupled to the first switch circuit.

18. The implantable medical device of claim 1, comprising a non-transitory tangible machine-readable medium including instructions that configure the implantable medical device to:
open the first switch circuit;
control the bridge circuit such that the bridge circuit is in a second mode; and
close the switch circuit such that an opposite polarity energy is provided to the heart through the bridge circuit.

19. The implantable medical device of claim 1, comprising a non-transitory tangible machine-readable medium including instructions that configure the implantable medical device to:

determine whether an arrhythmia is present in the heart before delivering the first polarity energy; and determine whether the arrhythmia remains present before delivering the opposite polarity energy.

20. An implantable medical device for delivering electric therapy to a heart of a patient, comprising:
a defibrillation voltage source;
a first switch circuit comprising a first node and a second node, the first node coupled to a first terminal of the voltage source;
a bridge circuit coupled to the second node and to a second terminal of the voltage source, the bridge circuit configured to connect to a first electrode and a second electrode, the first and second electrodes configured to be implanted in or near the heart;
wherein the bridge circuit is configured to deliver a first polarity energy to the heart using the first and second electrodes in a first mode, and the bridge circuit is configured to deliver an opposite polarity energy to the heart using the first and second electrodes in a second mode; and
wherein closing the first switch circuit comprises charging a drive voltage capacitor coupled to a gate and an emitter of a transistor, the transistor comprising a collector coupled to the first terminal of the voltage source and the emitter coupled to the bridge circuit, causing the drive voltage capacitor to provide a voltage to turn on the transistor;
wherein the first switch circuit is configured to control a timing of the delivery of the first polarity energy and the opposite polarity energy;
wherein the bridge circuit comprises:
a second switch circuit coupled to the second node and configured to be connected to the first electrode;
a third switch circuit coupled to the second node and configured to be connected to the second electrode;
a fourth switch circuit coupled to the second terminal and configured to be connected to the first electrode;
a fifth switch circuit coupled to the second terminal and configured to be connected to the second electrode; and
wherein the bridge circuit is configured to deliver the first polarity energy when the third and fourth switch circuits are closed, and wherein the bridge circuit is configured to deliver the opposite polarity energy when the second and fifth switch circuits are closed.

21. The implantable medical device of claim 20, wherein the second, third, fourth, and fifth switch circuits comprise thyristors, and wherein the second and fourth switch circuits are stacked substantially adjacent to each other.

* * * * *

UNITED STATES PATENT AND TRADEMARK OFFICE
CERTIFICATE OF CORRECTION

PATENT NO. : 8,116,865 B2
APPLICATION NO. : 12/332497
DATED : February 14, 2012
INVENTOR(S) : William J. Linder et al.

Page 1 of 1

It is certified that error appears in the above-identified patent and that said Letters Patent is hereby corrected as shown below:

On the Title Page, Item (73), in "Assignee", line 1, delete "Cardiac Pacemarkers, Inc.," and insert -- Cardiac Pacemakers, Inc., --, therefor.

Signed and Sealed this
Second Day of October, 2012

David J. Kappos
*Director of the United States Patent and Trademark Office*